United States Patent [19]

Heywang et al.

[11] Patent Number: 4,599,349
[45] Date of Patent: Jul. 8, 1986

[54] CARBAMOYLATED AZOLYLALKYL-PHENOXY-CARBINOLS AND THEIR USE AS PLANT-PROTECTION AGENTS

[75] Inventors: Gerhard Heywang, Bergisch-Gladbach; Paul Reinecke, Leverkusen; Wilhelm Brandes, Leichlingen; Gerd Haenssler, Leverkusen; Ingeborg Hammann, Muehlheim, all of Fed. Rep. of Germany

[73] Assignee: Bayer Aktiengesellschaft, Leverkusen, Fed. Rep. of Germany

[21] Appl. No.: 597,777

[22] Filed: Apr. 6, 1984

[30] Foreign Application Priority Data

Apr. 27, 1983 [DE] Fed. Rep. of Germany ....... 3315262

[51] Int. Cl.[4] .................... A01N 47/22; C07D 405/12
[52] U.S. Cl. .................................... 514/383; 548/101; 548/262; 548/336
[58] Field of Search ................. 548/262, 336; 424/269, 424/273 R; 514/383

[56] References Cited

U.S. PATENT DOCUMENTS 4,145,428  3/1979  Kramer et al. ........................ 424/269
4,153,692  5/1979  Kramer et al. ........................ 548/341
4,237,142 12/1980  Buchel et al. ........................ 424/245
4,239,766 12/1980  Kramer et al. ........................ 424/245
4,254,132  3/1981  Kramer et al. ........................ 548/341
4,367,089  1/1983  Adams ..................................... 71/76

FOREIGN PATENT DOCUMENTS 0044994  2/1982  European Pat. Off. ............ 548/262

Primary Examiner—Alton D. Rollins
Attorney, Agent, or Firm—Sprung, Horn, Kramer & Woods

[57] ABSTRACT

Carbamoylated azolylalkyl-phenoxy-carbinols of the formula

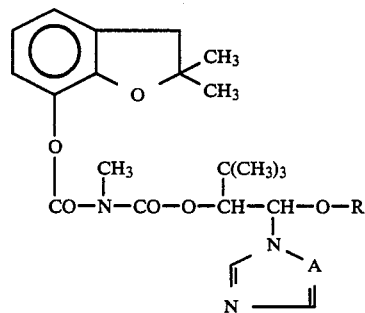

in which
A is a nitrogen atom or the CH group, and
R is optionally substituted phenyl, which possess fungicidal and insecticidal activity.

5 Claims, No Drawings

CARBAMOYLATED AZOLYLALKYL-PHENOXY-CARBINOLS AND THEIR USE AS PLANT-PROTECTION AGENTS

The present invention relates to new carbamoylated azolylalkyl-phenoxy-carbinols, a process for their preparation and their use as plant-protection agents.

It has already been disclosed that certain carbamoylated 3,3-dimethyl-1-phenoxy-1-(1,2,4-triazol-1-yl)-2-butanols, such as, for example, 1-(4-biphenylyloxy)-3,3-dimethyl-2-methoxycarbonylcarbamoyloxy-1-(1,2,4-triazol-1-yl)butane or 1-(4-biphenylyloxy)- or 1-(2,5-dichlorophenoxy)- or 1-(2,4,5-trichlorophenoxy)-3,3-dimethyl-2-methylcarbamoyloxy-1-(1,2,4-triazol-1-yl)butane have good fungicidal properties (compare U.S. Pat. No. 4,145,428 issued 3/20/79 and U.S. Pat. No. 4,380,682 issued 4/19/83). However, the effect of these compounds in certain areas of indication, especially when low quantities and concentrations are applied, is not always entirely satisfactory.

New carbamoylated azolylalkyl-phenoxy-carbinols of the general formula

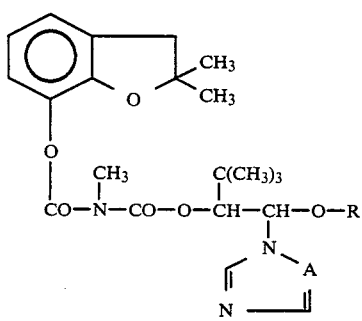

in which
A represents a nitrogen atom or the CH group, and
R represents optionally substituted phenyl, have been found.

The compounds of the formula (I) have two asymmetric carbon atoms; thus they can exist in two geometric isomers (threo and erythro forms). They principally result as mixtures of the two forms.

In addition, it has been found that the carbamoylated azolylalkyl-phenoxy-carbinols of the formula (I) are obtained by reacting, in the presence of a diluent and in the presence of an acid-binding agent, 1-azolyl-3,3-dimethyl-1-phenoxy-2-butanols of the formula

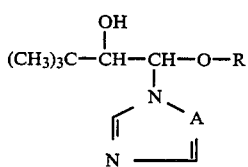

in which
A and R have the meaning indicated above, with N-(2,3-dihydro-2,2-dimethyl-benzofuran-7-oxy-carbonyl)-N-methyl-carbamoyl halides of the formula

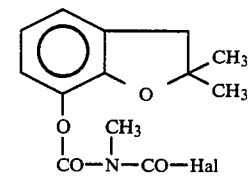

in which
Hal represents a halide, preferably chlorine or bromine.

It is possible, where appropriate, subsequently to add an acid or a metal salt to the compounds of the formula (I) thus obtained.

The new carbamoylated azolylalkyl-phenoxy-carbinols of the formula (I) have strong fungicidal and insecticidal properties. In this context, surprisingly, the compounds according to the invention exhibit a better fungicidal and a better insecticidal effect than the carbamoylated 3,3-diethyl-1-phenoxy-1-(1,2,4-triazol-1-yl)-2-butanols known from the state of the art, such as 1-(4-biphenylyloxy)-3,3-dimethyl-2-methoxycarbonylcarbamoyloxy-1-(1,2,4-triazol-1-yl)butane or 1-(4-biphenylyloxy)- or 1-(2,5-dichlorophenoxy)- or 1-(2,4,5-trichlorophenoxy)-3,3-dimethyl-2-methylcarbamoyloxy-1-(1,2,4-triazol-1-yl)butane, which are compounds of closely related structure and effects. Thus, the substances according to the invention are an enrichment of technology.

The carbamoylated azolylalkyl-phenoxy-carbinols according to the invention are generally defined by the formula (I). In this formula,
A preferably represents a nitrogen atom or the CH group, and
R preferably represents phenyl which is optionally monosubstituted or disubstituted, identically or differently, substituents which may be mentioned being: halogen, alkyl having 1 to 4 carbon atoms and phenyl which is optionally substituted by halogen.

Those compounds of the formula (I) in which
A represents a nitrogen atom or the CH group, and
R represents phenyl substituted by fluorine, chlorine, methyl or phenyl
are particularly preferred.

Those compounds of the formula (I) in which
A represents a nitrogen atom, and
R represents phenyl substituted by fluorine, chlorine or phenyl
are very particularly preferred.

When, for example, 1-(4-chlorophenoxy)-3,3-dimethyl-1-(1,2,4-triazol-1-yl)-2-butanol and N-2,3-dihydro-2,2-dimethyl-benzofuran-7-oxy-carbonyl)-N-methyl-carbamoyl chloride are used as the starting materials, then the course of the reaction in the process according to the invention can be represented by the diagram below:

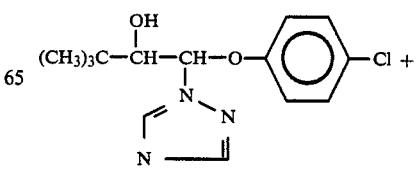

-continued

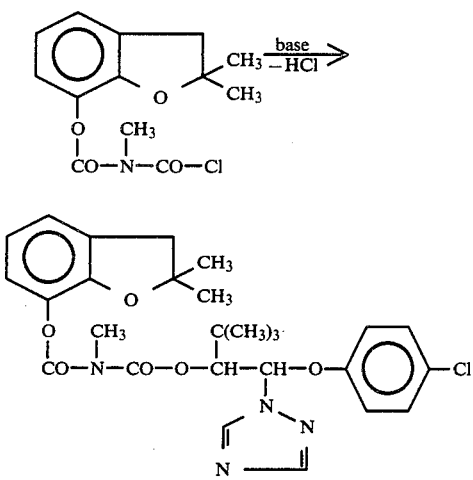

The 1-azolyl-3,3-dimethyl-1-phenoxy-2-butanols necessary as starting materials to carry out the process according to the invention are generally defined by the formula (II). In this formula, A and R preferably represent the meanings which have already been mentioned in the description of the substances of the formula (I) according to the invention as being preferred for these radicals.

The 1-azolyl-3,3-dimethyl-1-phenoxy-2-butanols of the formula (II) are known (compare U.S. Pat. No. 3,952,002 issued 4/20/76 and U.S. Pat. No. 3,940,414 issued 2/24/76) and can be obtained in a customary manner using the processes indicated there by reduction of the corresponding keto derivatives.

The N-(2,3-dihydro-2,2-dimethyl-benzofuran-7-oxycarbonyl)-N-methyl-carbamoyl halide of the formula (III) which is also to be used as starting material for the process according to the invention is likewise known (compare DE-OS (German Published Specification) No. 2,142,496 [Le A 13 913] and U.S. Pat. No. 4,211,790).

Suitable diluents for the process according to the invention are inert organic solvents. These preferably include aromatic hydrocarbons, such as benzene or toluene; halogenated hydrocarbons, such as methylene chloride or carbon tetrachloride; nitriles, such as acetonitrile or propionitrile; ethers, such as tetrahydrofuran or dioxane; and esters, such as methyl acetate.

All customary organic and inorganic acid-binders can be employed as the acid-binding agent for the process according to the invention. These preferably include tertiary amines, such as triethylamine; alkali metal hydroxides and alkali metal carbonates, such as sodium hydroxide and potassium hydroxide.

On carrying out the process according to the invention, it is possible to vary the reaction temperatures in a relatively wide range. In general, the process is carried out between 0° and 100° C., preferably between 20° and 85° C.

On carrying out the process according to the invention, equimolar amounts are preferably used. The isolation of the final products is carried out in a generally customary manner.

The following acids are suitable and preferable for the preparation of physiologically tolerated acid addition salts of the compounds of the formula (I): hydrogen halide acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicyclic acid, sorbic acid and lactic acid, and sulphonic acids, such as, for example p-toluenesulphonic acid and 1,5-naphthalenesulphonic acid.

The acid addition salts of the compounds of the formula (I) can be obtained in a simple manner by customary salt formation methods, for example by dissolving a compound of the formula (I) in a suitable inert solvent and adding the acid, for example hydrogen chloride, and they can be isolated in a known manner, for example by filtration, and if appropriate purified by washing with an inert organic solvent.

Salts of metals of main groups II and IV and of subgroups I and II and IV to VIII are preferably used for the preparation of metal salt complexes of the compounds of the formula (I), examples of metals which may be mentioned being copper, zinc, manganese, magnesium, tin, iron and nickel. Possible anions of the salts are those which are preferably derived from the following acids: hydrogen halide acids, such as, for example, hydrochloric acid and hydrobromic acid, and furthermore phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As fungicides, the active compounds according to the invention can be used with particularly good success for combating powdery mildew of cereals (*Erysiphe graminis*), powdery mildew of cucumber (*Spaerotheca fuliginea*) and rice diseases, such as *Pellicularia sasakii;* furthermore, the active compounds according to the invention can be employed as shoot fungicides against rust, *Septoria nodorum, Cochliobolus sativus* and *Pyrenophora teres*, and as seed-dressing agents against stripe disease of barley (*Drechslera graminea*), snow mould (*Fusarium nivale*) and *Fusarium culmorum* on cereals.

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp.. From the order of the Anoplura, for example, *Phylloxera vastatrix*, Pemphigus spp., *Pediculus humanus corporis*, Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aenus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*. From the order of the Siphonaptera, for example, *Xenopsylla cheopis* and Ceratophyllus spp. From the order of the Arachnida, for example, *Scorpio maurus* and *Latrodectus mactans*. From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

As insecticides, the active compounds according to the invention can be used with particularly good success for combating *Doralis fabae* and *Phaedon larvae*. In addition, the good action as a soil insecticide and the good root-systemic action should be singled out.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketones, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs and azole-metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

When the substances according to the invention are used as fungicides, the amount used can be varied within a relatively wide range, depending on the type of application. Thus, in the treatment of parts of plants, the active compound concentrations in the use forms are in general between 1 and 0.0001% by weight, preferably between 0.5 and 0.001% by weight. In the treatment of seed, amounts of active compound of 0.001 to 50 g per kg of seed, preferably 0.01 to 10 g, are generally required. In the treatment of the soil, active compound concentrations of 0.00001 to 0.1% by weight, preferably 0.0001 to 0.2%, are required at the place of action.

When the substances according to the invention are used as insecticides, too, the content of active compound in the use forms prepared from the commercial formulations can vary within wide ranges. The active compound concentration of the use forms can be from 0.0000001 to 100% % by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates (substrates coated with lime).

The preparation and use of the substances according to the invention are illustrated by the examples which follow.

PREPARATION EXAMPLE

EXAMPLE 1

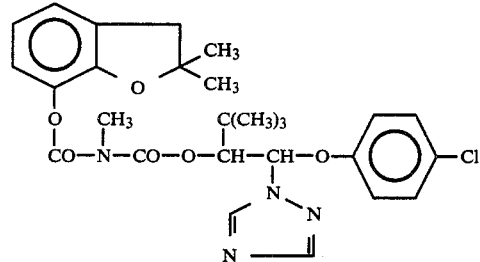

5.9 g (0.017 mole) of 1-(4-chlorophenoxy)-3-3-dimethyl-1-(1,2,4-triazol-1-yl)-2-butanol and 4.8 g (0.017 mole) of N-(2,3-dihydro-2,2-dimethyl-benzofuran-7-oxy-carbonyl)-N-methyl-carbamoyl chloride are suspended in 50 ml of toluene, and 2.4 ml (0.017 mole) of triethylamine are added dropwise with stirring. The reaction mixture is allowed to stir overnight and the precipitate is then filtered off. The filtrate is washed with water, dried over sodium sulphate and evaporated. 8 g (87% of theory) of 1-(4-chlorophenoxy)-3,3-dimethyl-2-[N-(2,3-dihydro-2,2-dimethyl-benzofuran-7-oxycarbonyl)methylcarbamoyloxy]-1-(1,2,4-triazol-1-yl)butane of refractive index $n_D^{20} = 1.5360$ are obtained.

USE EXAMPLES

In the examples which follow, the compounds indicated below are employed as comparison substances:

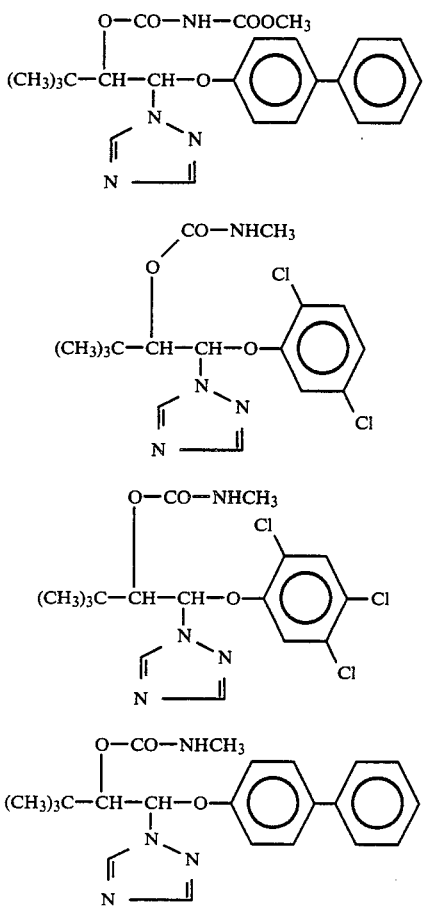

EXAMPLE A

Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compound according to Example 1.

EXAMPLE B

Erysiphe test (barley)/seed treatment

The active compounds are used as dry dressings. These are prepared by extending the particular active compound with a ground mineral to give a finely pulverulent mixture, which ensures uniform distribution on the seed surface.

To apply the dressing, the seed is shaken with the dressing in a closed glass flask for 3 minutes.

3 batches of 12 grains of the barley are sown 2 cm deep in standard soil. 7 days after sowing, when the young plants have unfolded their first leaf, they are dusted with spores of Erysiphe graminis f. sp. hordei.

The plants are placed in a greenhouse at a temperature of about 20° C. and a relative atmospheric humidity of about 80% in order to promote the development of powdery mildew pustules.

Evaluation is carried out 7 days after the inoculation.

In this test, a clearly superior activity compared with the prior art is shown, for example, by the compound according to Example 1.

EXAMPLE C

Sphaerotheca test (cucumber)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea.*

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compound according to Example 1.

EXAMPLE D

Pellicularia test (rice)

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3 to 4 leaf stage are sprayed until dripping wet. The plants remain in a greenhouse until they have dried off. The plants are then inoculated with Pellicularia sasakii and are placed at 25° C. and 100% relative atmospheric humidity.

The evaluation of the disease infestation is carried out 5 to 8 days after the inoculation.

In this test, a clearly superior activity compared with the prior art is shown, for example, by the compound according to Example 1.

EXAMPLE E

Doralis test (systemic action)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Vicia faba*) which have been heavily infested with the bean aphid (*Doralis fabae*) are each watered with 20 ml of the preparation of the active compound in such a way that the preparation of the active compound penetrates into the soil without wetting the leaves of the bean plants. The active compound is taken up from the soil by the bean plants and thus passes to the infested leaves.

After the specified period of time, the destruction in % is determined. 100% means that all the aphids have been killed.

In this test, for example, the compound from Example 1 shows a superior activity compared to the prior art.

EXAMPLE F

Phaedon larvae test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infected with mustard beetle larvae (*Phaedon cochleariae*), as long as the leaves are still moist.

After the specified period of time, the destruction in % is determined. 100% means that all the larvae have been killed; 0% means that none of the larvae have been killed.

In this test, for example, the compound from Example 1 shows a superior activity compared to the prior art.

It will be appreciated that the instant specification and examples are set forth by way of illustration and not limitation, and that various modifications and changes may be made without departing from the spirit and scope of the present invention.

We claim:

1. A carbamoylated azolylalkylphenoxy-carbinol of the formula

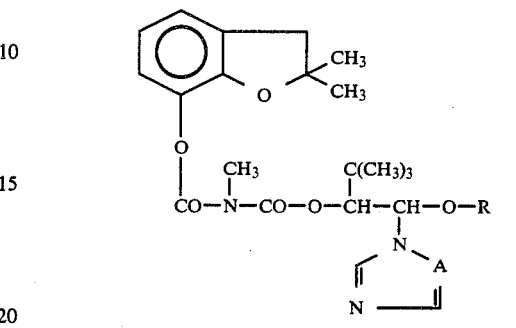

in which
A is a nitrogen atom and
R is phenyl substituted by fluorine, chlorine, methyl or phenyl.

2. A compound according to claim 1, wherein such compound is 1-(4-chlorophenoxy)-3,3-dimethyl-2-[N-(2,3-dihydro-2,2-dimethylbenzofuran-7-oxy-carbonyl)-methylcarbamoyloxy]-1-(1,2,4-triazol-1-yl)butane of the formula

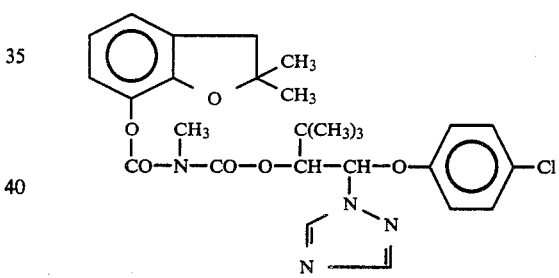

3. A fungicidal and insecticidal composition comprising a fungicidally and insecticidally effective amount of a compound according to claim 1 in admixture with a diluent.

4. A method of combatting fungi and insects which comprises administering to such fungi and insects, or to a habitat thereof, a fungicidally and insecticidally effective amount of a compound according to claim 1.

5. A method of combatting fungi and insects which comprises administering to such fungi and insects, or to a habitat thereof, a fungicidally and insecticidally effective amount of a compound according to claim 2.

* * * * *